United States Patent [19]

Hein

[11] Patent Number: 6,159,472
[45] Date of Patent: Dec. 12, 2000

[54] INTRADERMAL AVIAN IMMUNIZATION WITH INACTIVATED VACCINES

[75] Inventor: Rudolf George Hein, Georgetown, Del.

[73] Assignee: Akzo Nobel N.V., Arnhem, Netherlands

[21] Appl. No.: 09/192,655

[22] Filed: Nov. 16, 1998

[51] Int. Cl.[7] .......................... A61K 39/00; A61K 39/12; A61K 39/15
[52] U.S. Cl. .................................... 424/184.1; 424/204.1; 424/215.1
[58] Field of Search .............................. 424/184.1, 204.1, 424/215.1; 435/236, 238

[56] References Cited

U.S. PATENT DOCUMENTS 2,512,882  6/1950  Truesdale .
4,795,635  1/1989  Peleg et al. ................................ 424/89
4,990,135  2/1991  Truesdale .
5,686,077  11/1997  Schrier .
5,728,569  3/1998  Schrier .

OTHER PUBLICATIONS

Hassan et al., Avian Diseases 40:567–571, 1996.
Giambrone et al., Poultry Science 65:457–461, 1986.

*Primary Examiner*—Anthony C. Caputa
*Assistant Examiner*—Brenda G. Brumback
*Attorney, Agent, or Firm*—William M. Blackstone

[57] ABSTRACT

The present invention relates to methods for immunizing birds using small volumes of vaccine. According to the invention, effective immunization can be accomplished with small, relatively concentrated quantities of inactivated vaccine administered by intradermal means.

7 Claims, No Drawings

INTRADERMAL AVIAN IMMUNIZATION WITH INACTIVATED VACCINES

DESCRIPTION OF THE INVENTION

The present invention relates to methods for immunizing birds using small volumes of inactivated antigen in vaccines. According to the invention, effective immunization can be accomplished with small, relatively concentrated quantities of inactivated vaccine administered by intradermal means.

BACKGROUND OF THE INVENTION

Vaccines have been administered to birds by injection intradermally, such as in the wing web, intramuscularly, such as in the breast muscle, or subcutaneously, such as in the neck. Administration intradermally in the wing web has always been limited to use with live vaccines, as only a small volume can be administered and, because live vaccines have to multiply after administration, it was thought that only they, by multiplication, presented sufficient antigen to achieve immunization. Larger quantities of vaccine can be administered subcutaneously and, most easily, intramuscularly, and these are the methods presently used for administering vaccines comprising inactivated antigens. The volumes administered by these means are normally 0.1 to 1 ml, most usually in the range of 0.2 to 0.5 ml. When administered in amounts of from 0.2 to 0.5 ml, avian vaccines commonly contain multiple inactivated immunogens. In some instances a live vaccine is mixed into an inactivated vaccine liquid formulation prior to administration. In which case the inactivated vaccine solution is used as the carrier. An example of such live vaccines are CAV vaccines, also referred to as chicken anemia agent (CAA) vaccines, as described in U.S. Pat. Nos. 5,686,077 and 5,728,569, which are included herein by reference. CAV has been shown to act like an immune modulator when combined with the inactivated vaccine.

In the poultry industry, immunizing by intramuscular or subcutaneous administration of inactivated vaccines has drawbacks. Dealing with large numbers of birds, it is desired to use the smallest amount of vaccine and a vaccine that is easy and safe to administer, and yet achieve satisfactory protection. With intradermal administration in the wing web, handling the birds in easier and the likelihood of a needle stick to the person during the vaccination is reduced. This is especially true when compared to subcutaneous administration in the neck, with which "self vaccination" is common, resulting in injury and sometimes loss of fingers from infection. Another goal is to reduce the volume of vaccine administered, which reduces the volume of vaccine that must be handled. This increases the number of immunizations that can be made from a given volume of vaccine.

A principal goal of the invention is the reduction of product damage; that is, damage to muscle tissue. Intramuscular, and even subcutaneous, injections to food animals can cause areas of inflammation, which result in stress to the animal and damage to the meat. A stressed animal will not feed or grow as well as a non-stressed animal. Moreover, using conventional amounts of vaccine the site of a localized immune response may remain as permanently damaged tissue. There is also the problem of vaccine retention, with vaccine remaining at the site of injection long after the vaccine is administered. For these reasons, the birds cannot normally be sold to the food industry.

Using the small volumes according to the invention minimizes localized inflammation and eliminates residual vaccine remaining at the site of injection.

Until the present invention, only live vaccines have been administered using intradermal administration to the wing web of chickens. Diseases for which this method has been used include Fowl Pox, Pigeon Pox, Fowl Cholera, Reo virus, Newcastle disease virus, Chicken Anemia virus (CAA or CAV) and Avian Encephalomyelitis (AE). The GRANT™ inoculator sold by International Inoculation Systems, Inc. of Cary, N.C., is advertised for wing web administration of vaccines in quantities of as little as 0.008 ml. These inoculators are described and claimed in U.S. Pat. No. 4,990,135, which is included herein by reference.

Prior to the present invention, inactivated vaccines have not been administered to the wing web because it has always been believed that inactivated vaccines must be administered subcutaneously or intramuscularly and with sufficient adjuvant in order to achieve an effective immune response. The small volumes used in wing web administration were not expected to accommodate a sufficient amount of adjuvant to present the immunogen for an adequate immune response and protective immunity.

We have discovered that inactivated vaccines can be administered intradermally into the wing web in volumes of from about 0.004 to about 0.08 ml with good results. Effective immunization can be accomplished administering these small volumes of vaccine if the total quantity of antigen per dose is at least one third the quantity in the large volumes previously used for administering inactivated vaccines by intramuscular means. Surprisingly, large quantities of adjuvant were not necessary for successful results.

When intradermal administration was used for live vaccines, it has always been necessary to separately vaccinate the same bird again in a different way if inactivated vaccines were to be administered. Reducing the number of immunizations each bird receives is a goal of significant economic interest. This is accomplished according to the invention by using a combination vaccine, which may contain both live and killed immunogens, administered via the wing web.

SUMMARY OF THE INVENTION

The present invention relates to vaccines comprising inactivated immunogens in concentrations sufficiently high that single doses of 0.004 to about 0.08 ml provide effective immunity from avian diseases. It also relates to methods for protecting birds against avian diseases through intradermal immunization with vaccines comprising inactivated immunogens.

DETAILED DESCRIPTION OF PREFERRED EMBODIMENTS

Because producers have been concerned about vaccine reactions from inactivated products following subcutaneous administration in the neck and intramuscular administration in the breast or thigh, an alternate route was sought. Although it was believed in the industry that insufficient antigen and adjuvant could be administered through the wing web/intradermal (ww/id) route to give protection using inactivated vaccines, we decided to pursue it because there would be no adverse tissue reaction or vaccine residue in the meat and the vaccine could easily be applied by this route. This is also a safer method for the worker administering the vaccine, as he is less likely to stick himself than when vaccinating in the neck. In the following example we show that concentrating the inactivated antigen to 0.03 ml doses and administering the vaccine via the wing web route results in a satisfactory serological response four to eight weeks after vaccination.

With this invention effective immunization can be achieved using small volume doses of inactivated vaccine administered intradermally through the wing web. Unexpectedly, inactivated vaccines can be administered this way and effective protection achieved even though the quantity of adjuvant is reduced in proportion to the reduction in vaccine doze size. Single immunogen vaccines can be used; however, it is preferred to reduce the number of immunizations necessary and combination multivalent vaccines are preferred. It is also intended to use combination vaccines containing both inactivated and live immunogens in the method of the invention.

Vaccines administered according to the invention will comprise inactivated immunogens and adjuvants. Examples of adjuvants that may be used are mineral oil (e.g., MARCOL™ and DRAKEOL™, Penreco, both available from Van Waters & Rogers) with emulsifiers (e.g., TWEEN 20™, TWEEN 80™, and SPAN80™, ICI America, available from van Waters and Rogers), tocols (e.g., Vitamin E) and vegetable oils, such as coconut oil and soy bean oil. Any commercial adjuvants known to the skilled artisan may be used. Examples of these include CARBIGEN™ (MVP Laboratories, Inc.), MONTANIDE ISA70™ (SEPPIC), EMULSIGEN™ (MVP Laboratories, Inc.) REHYDRAGEL™ (Reheis), and combinations of two or more of these.

Inactivated immunogens that may be used in vaccines according to the invention include Infectious Bursal Disease virus (IBDV), Reovirus, Newcastle Disease virus (NDV), infectious bronchitis virus (IBV), EDS, TRT, avian influenza (AI), Avian Encephalomyelitis (AE) and Chicken Anemia virus (CAA, CAV, CIA). Any other poultry disease vaccines that can be used in inactivated form for immunization will also be effective in small volume doses and are intended to be included within the present invention. These include bacterial antigens, especially subunit vaccines (e.g., *E. coli* vaccines), as well as bacterial whole cell vaccines.

The vaccines in a preferred embodiment are intended to also comprise live strains of disease organisms, preferably modified strains. It is intended that all conventional live immunogens can be administered according to the invention in combination with killed immunogens. Examples include CAV, AE and Fowl Pox, which are already administered in the wing web as modified live vaccines, but have not previously been used in combination with inactivated immunogens. In a most preferred embodiment, the inactivated immunogens are combined with live CAV, which may also act as an immune modulator, and with mineral oil and emulsifiers to prepare the vaccine. Another embodiment is the same combination with tocols or vegetable oils in place of the mineral oil and emulsifier.

The vaccine compositions can be administered intradermally by any conventional means, including the conventional double needle inoculator or the automatic wing stab inoculator, or using gun-type type inoculators, through the wing stab method. The GRANT™ inoculator, as described in U.S. Pat. No. 4,990,135, and the TRUESDALE™ inoculator, described in U.S. Pat. No. 2,512,882 are examples of inoculators that may also be used.

The total volume administered according to the invention may range from about 0.08 to 0.004 ml, determined by the concentration of antigen in the dose. When formulating a vaccine to be used according to the invention, the total quantity of antigen administered is most preferred to be the same as administered conventionally through intramuscular and subcutaneous injection preferably at least one half, and minimally at least one third the quantity conventionally used. Thus, for example, if 0.1 ml of vaccine has been conventionally administered intramuscularly, and 0.01 ml will be administered by wing web, the concentration of antigen will be at least three, preferably five, and most preferably ten times as high in the vaccine to be used according to the invention.

In the examples we used a volume of 0.03 ml/dose because we found that 0.03 ml of the vaccine with a mineral oil adjuvant was the volume applied using the available wing web needle. Smaller volumes may be used as long as an adequate dose can be introduced.

The reduction in volume in vaccines according to the invention results in a proportional reduction in adjuvant. For example, the conventional dose of a vaccine in a water-in-oil emulsion is 0.5 ml. This is reduced to 0.03 ml according to the invention. Accordingly, 0.47 ml of liquid is deleted from the formula, and this is all essentially adjuvant emulsion.

The following examples show that a protective immune response is generated by vaccinating in the wing web with inactivated IBDV and reovirus, even without priming. In the preferred embodiment, the birds are primed with a live vaccine at one to two weeks of age.

EXAMPLE 1

Antibody titers measured by ELISA (enzyme immunoassay from IDEXX Laboratories, Inc., Westbrook, Me.) and VN (micro-virus neutralization test in chicken embryo fibroblasts using IBDV D-78® and reovirus S1133 as antigen (300–1000 $TCID_{50}$)) in chickens vaccinated with inactivated vaccines by the wing web route according to the invention were compared to those of chickens vaccinated with inactivated BREEDERVAC-REO PLUS®, (Intervet Inc., Millsboro, Del.; IBDV Variant E, Variant A, D-78®, GLS and Reovirus 1733 and 2408) administered via the intramuscular route in the breast in chickens (see Table 6). The chickens were both primed and not primed with D-78® (Intervet Inc., Millsboro, Del. (live IBDV)) or TENSYNVAC® (Intervet Inc., Millsboro, Del. (live reovirus)). The BREEDERVAC-REO PLUS® serial was prepared from the same antigen serials used for the inactivated vaccine prepared according to this invention (vaccine A). Vaccine A was a prototype containing the same immunogens as BREEDERVAC-REO PLUS® with the exception that vaccine A did not contain IBDV Variant A and contained a lower concentration of other antigens. The content per dose for each vaccine is given in Table 6.

Trial Design

Sixty (60) one-day old specific pathogen free (SPF) chickens were obtained from Spafas, Inc., Norwich, Conn., divided into six groups, and placed in negative pressure isolators (Table 1). At seven days of age half of the groups were vaccinated by the subcutaneous route (SC) in the back of the neck, midway between the head and body with a full dose (0.2 ml) of live TENSYNVAC® (isolators 1, 3 and 5). The other three groups were vaccinated at 14 days of age with a full dose (0.03 ml) of live D-78® via eye drop (isolators 2, 4 and 6). Two groups, one primed with TENSYNVAC® and one primed with D-78®, as described above, were vaccinated intramuscularly (IM) in the breast at six weeks of age with a full dose (0.5 ml) of inactivated BREEDERVAC-REO PLUS® (isolators 3 and 4). Two of the groups primed with TENSYNVAC® and two of the groups primed with D-78® were administered inactivated prototype vaccine A according to the invention by the wing web route using the wing stabber (isolator 1). These vaccines contained the inactivated antigens, IBDV (Variant E, D-78® and GLS) and reovirus strains 1733 and 2408. Vaccine A did not include Variant A IBDV, although BREEDERVAC-REO PLUS® did (B). Prototype vaccine A was prepared with mineral oil (47% by weight) and emulsifiers (7.9% by weight) forming a water-in-oil emulsion. 30 ml of vaccine provided 1000 doses. The compositions and concentrations of the various antigens in the prototype vaccine A and inactivated BREEDERVAC-REO PLUS® are shown in Table 6.

Prior to vaccination at 6 weeks, 10 weeks and 14 weeks of age, all chickens were bled and serum was tested for antibodies against IBDV and reovirus using the ELISA (Idexx, Westbrook, Me.) and/or VN methods (CEF using IBDV D-78® and reovirus S 1133).

Results and Discussion

The reovirus and IBDV ELISA geometric mean titers (GMT) and coefficients of variation (CVs) are summarized in Tables 2 and 3, respectively. Tables 4 and 5 summarize the IBDV and reovirus virus neutralization (VN) GMTs.

Reovirus Antibody Response (Tables 2 and 5)

Without reovirus priming at one week of age, the prototype vaccine according to the invention (A) administered by the wing web route at six weeks of age did not produce a significant serologic response to reovirus, as measured by the ELISA test four and eight weeks post-vaccination (isolator 2). With reovirus priming at one week, wing web vaccination with the prototype vaccine A containing mineral oil and emulsifiers as adjuvant showed a significant titer increase, particularly in the VN test. Even though traditional IM vaccination using 0.5 ml of Breedervac-Reo Plus® (live vaccine) induced a higher antibody titer, especially with the ELISA (isolator 3), wing web vaccination with 0.03 ml of vaccine A, provided acceptable responses when primed at one week of age for reovirus using a live vaccine, which is the common practice under field conditions (isolator 1).

IBDV Antibody Response (Tables 3 and 4)

The IBDV VN titers of chickens primed with D-78® increased following the administration of prototype vaccines administered by the wing web route (isolator 2), although these titers were not quite as high as in chickens primed with D-78 followed by administration of BREEDERVAC-REO PLUS® given by the IM route (isolator 4). In non-prized chickens prototype vaccine A induced significant titers (isolator 1), although lower than those of chickens vaccinated with BREEDERVAC-REO PLUS® administered by the IM route (isolator 3).

The wing web route of administration showed an antibody response using small volumes of inactivated IBDV and reovirus antigens. An inactivated vaccine administered by the wing web route containing a similar amount of inactivated antigens with a mineral oil adjuvant in a 0.03 ml done is shown to be an acceptable alternative to the IM route of administration with the current 0.5 ml volume of the BREEDERVAC-REO PLUS® vaccine.

TABLE 1

Summary of Trial Design

| GROUP | TENSYNVAC ®* @ 7 DAY | D-78 ®* @ 14 DAY | 6 WEEK VACCINE | ROUTE |
|---|---|---|---|---|
| 1 | YES | NO | Prototype A (Mineral Oil/ Emulsifier Adjuvant + Antigens) | WW |
| 2 | NO | YES | Prototype A (Mineral Oil/ Emulsifier + Antigens) | WW |
| 3 | YES | NO | BREEDER-VAC-REO PLUS ®* | IM |
| 4 | NO | YES | BREEDER-VAC-REO PLUS ®* | IM |
| 5 | YES | NO | NONE | — |
| 6 | NO | YES | NONE | — |

*Intervet Inc., Millsboro, DE

TABLE 2

Reovirus ELISA Geometric Mean Titers and CVs
Prevaccination and Four and Eight Week Post-Vaccination

| ISOLATOR | TENSYNVAC ® (Reovirus) 5/1/97 | D-78 ® (IBDV) 5/8/97 | INACT VAC 6/6/97 | 6/5/97 GMT | CV | 7/3/97 GMT | CV | 8/1/97 GMT | CV |
|---|---|---|---|---|---|---|---|---|---|
| 1 | X | | A | 1848 | 42.1 | 2371 | 58.7 | 2236 | 44.6 |
| 2 | | X | A | 24 | 225.8 | 44 | 104.3 | 3 | 247.3 |
| 3 | X | | B | 795 | 95.3 | 8269 | 50.1 | 7920 | 60.0 |
| 4 | | X | B | 31 | 131.5 | 1189 | 73.8 | 4632 | 49.5 |
| 5 | X | | — | 1074 | 34.3 | 1002 | 96.5 | 628 | 49.7 |
| 6 | | X | — | 96 | 75.6 | 86 | 62.5 | 26 | 109.2 |

A = Vaccine containing inactivated antigens, mineral oil, and emulsifiers concentrated to 0.03 ml/dose administered via wing-web route
B = BREEDERVAC-REO PLUS ® administered intramuscularly (0.5 ml) in the breast

TABLE 3

IBDV ELISA Geometric Mean Titers and CVs Prevaccination
and Four and Eight Weeks Post-Vaccination

| ISOLATOR | TENSYNVAC ® (Reovirus) 5/1/97 | D-78 ® (IBDV) 5/8/97 | INACT VAC 6/6/97 | 6/5/97 GMT | 6/5/97 CV | 7/3/97 GMT | 7/3/97 CV | 8/1/97 GMT | 8/1/97 CV |
|---|---|---|---|---|---|---|---|---|---|
| 1 | X |   | A | 42 | 141 | 1800 | 27.2 | 1443 | 46.5 |
| 2 |   | X | A | 4085 | 45.2 | 5564 | 21.5 | 4022 | 29.8 |
| 3 | X |   | B | 18 | 249.8 | 3725 | 45.6 | 4554 | 45.4 |
| 4 |   | X | B | 2836 | 22.7 | 4050 | 51.8 | 8761 | 23.9 |
| 5 | X |   | — | 15 | 211.5 | 55 | 95.3 | 100 | 52.8 |
| 6 |   | X | — | 3856 | 48.4 | 3020 | 36.8 | 1645 | 49.0 |

A = Vaccine containing inactivated antigens, mineral oil, and emulsifiers concentrated to 0.03 ml/dose administered via wing-web route
B = BREEDERVAC-REO PLUS ® administered intramuscularly (0.5 ml) in the breast

TABLE 4

IBDV VN Geometric Mean Titers (Log Base 2)
Prevaccination and Four and Eight Weeks Post-Vaccination

| ISO-LATOR | TENSYNVAC ® 5/1/97 | D-78 ® 5/8/97 | INACT VAC 6/6/97 | 6/5/97 GMT | 7/3/97 GMT | 8/1/97 GMT |
|---|---|---|---|---|---|---|
| 1 | X |   | A | nt$^2$ | 11.8 | 10.1 |
| 2 |   | X | A | 10.8 | $\geq$15.4 | 13.9 |
| 3 | X |   | B | nt$^2$ | 13.2 | 13.6 |
| 4 |   | X | B | 11.0 | $\geq$16.3 | $\geq$15.9 |
| 5 | X |   | — | <1 | <1 | <1 |
| 6 |   | X | — | 11.1 | 10.7$^1$ | 11.0 |

$^1$Highest dilution used $2^{16}$
$^2$nt - not tested

TABLE 5

Reovirus VN Geometric Mean Titers (Log Base 2)
Prevaccination and Four and Eight Weeks Post-Vaccination

| ISO-LATOR | TENSYNVAC ® 5/1/97 | D-78 ® 5/8/97 | INACT VAC 6/6/97 | 6/5/97 GMT | 7/3/97 GMT | 8/1/97 GMT |
|---|---|---|---|---|---|---|
| 1 | X |   | A | 3 | $\geq$6.8$^1$ | $\geq$6.4$^1$ |
| 2 |   | X | A | nt$^2$ | nt$^2$ | nt$^2$ |
| 3 | X |   | B | 1.9 | $\geq$7.9$^1$ | $\geq$7.7$^1$ |
| 4 |   | X | B | nt$^2$ | nt$^2$ | nt$^2$ |
| 5 | X |   | — | 2.4 | 2.2 | 3.7 |
| 6 |   | X | — | <1.0 | <1.0 | <1.0 |

$^1$Highest dilution used $2^8$
$^2$nt - not tested

TABLE 6

Comparison of antigen content per dose in the prototype
vaccine and the standard BREEDERVAC-REO PLUS ®

| Antigen | A* | Breedervac-Reo Plus ®$^2$ (B)* |
|---|---|---|
| IBDV Var 1084 E$^1$ | 10$^{4.7}$ EID$_{50}$** | 10$^{4.7}$ EID$_{50}$/dose** |
| IBDV D-78$^2$ | 10$^{7.8}$ TCID$_{50}$/dose**** | 10$^{8.1}$ TCID$_{50}$/dose |
| IBDV GLS$^3$ | 10$^{7.1}$ TCID$_{50}$/dose | 10$^{7.1}$ TCID$_{50}$/dose |
| IBDV Var 1084 A$^1$ | none | 10$^{4.39}$ EID$_{50}$/dose |
| Reo 1733$^1$ | 10$^{6.53}$ TCID$_{50}$/dose | 10$^{8.0}$ TCID$_{50}$/dose |
| Reo 2408$^1$ | 10$^{6.51}$ TCID$_{50}$/dose | 10$^{7.81}$ TCID$_{50}$/dose |
| Mineral Oil | 47% by weight*** | 47% by weight |
| Emulsifier | 7.9% by weight*** | 7.9% by weight |

*All titres measured before inactivation
**EID$_{50}$ = Embryo infective dose 50%
***Water-in-oil emulsion
****TCID = Tissue culture infective dose 50%
1. Source - University of Delaware
2. Source - Intervet Inc., Millsboro, DE
3. Source - University of Maryland

I claim:

1. A method for immunizing a bird, comprising providing a vaccine composition comprising an inactivated immunogen and administering an immunogenic amount of the vaccine to the bird, said vaccine composition being administered intradermally in a volume of from 0.004 to 0.08 ml.

2. The method of claim 1, wherein the vaccine composition is administered into the wing web of the bird.

3. The method of claim 1, wherein the vaccine comprises inactivated infectious bursal disease virus (IBDV).

4. The method of claim 1, wherein the vaccine comprises inactivated reovirus.

5. The method of claim 1, wherein the vaccine further comprises a live immunogen.

6. The method of claim 1, wherein the vaccine comprises an adjuvant.

7. The method of claim 6, wherein the adjuvant comprises mineral oil.

* * * * *